United States Patent [19]
Teoule et al.

[11] Patent Number: 5,514,540
[45] Date of Patent: May 7, 1996

[54] METHOD FOR DETECTING SPECIFIC NUCLEIC ACID SEQUENCES BY AMPLIFICATION IN HIGHLY DILUTE SOLUTION

[75] Inventors: Robert Teoule; Thierry Livache, both of Grenoble; Brigitte Fouque, Seyssins; Sylvie Sauvaigo, Grenoble, all of France

[73] Assignee: CIS Bio International, Saclay, France

[21] Appl. No.: 90,436

[22] Filed: Jul. 6, 1993

Related U.S. Application Data

[63] Continuation of Ser. No. 778,112, filed as PCT/FR90/00410, Jan. 12, 1990, abandoned.

[30] Foreign Application Priority Data

Jun. 12, 1989 [FR] France .................. 89 07710
Aug. 8, 1989 [FR] France .................. 89 10643

[51] Int. Cl.⁶ .............. C12Q 1/70; C12Q 1/68; C12P 19/34
[52] U.S. Cl. .................. 435/5; 435/6; 435/91.2
[58] Field of Search ................... 435/5, 6, 91.2

[56] References Cited

U.S. PATENT DOCUMENTS

| | | | |
|---|---|---|---|
| 4,257,774 | 3/1981 | Richardson et al. | 435/6 |
| 4,683,195 | 7/1987 | Mullis et al. . | |
| 4,683,202 | 7/1987 | Mullis et al. . | |
| 4,800,159 | 1/1989 | Mullis et al. . | |
| 4,824,776 | 4/1989 | Heller | 435/6 |

FOREIGN PATENT DOCUMENTS

| | | |
|---|---|---|
| 0231495 | 8/1987 | European Pat. Off. . |
| 0297379 | 1/1989 | European Pat. Off. . |
| 0310229 | 4/1989 | European Pat. Off. . |
| 0328829 | 8/1989 | European Pat. Off. . |
| 2202328 | 9/1988 | United Kingdom . |
| 8401174 | 3/1984 | WIPO . |

OTHER PUBLICATIONS

Becker–André et al., *Nucleic Acids Res.* 17(22), 9437–9446 (1989).

Sauvaigo et al., *Nucleic Acids Res.* 18(11), 3175–3183 (1990).

Mullis et al. (1987) Methods in Enzymology, vol. 155, pp. 335–350.

Johan Walberg et al, Proc. Natl. Acad. Sci. USA, vol. 87 (1990) pp. 6569–6573.

Nucleic Acids Research, vol. 17, No. 7, Apr. 1989, IRL Press, H. Voss, et al.: "direct genomic fluorescnet on–line sequencing and analysis using in vitro amplification of DNA", pp. 2517–2527.

Proc. Natl. acad. Sci. USA, vol. 85, Jan. 1988, D. R. Engelke et al.: "Direct sequencing of enzymatically amplified human genomic DNA", pp. 544–558.

*Primary Examiner*—W. Gary Jones
*Assistant Examiner*—Kenneth R. Horlick
*Attorney, Agent, or Firm*—Oblon, Spivak, McClelland, Maier & Neustadt

[57] ABSTRACT

A method for detecting specific nucleic acid sequences (a single sequence and/or a mixture of nucleic acid sequences) which are present in a biological sample, comprising at least one enzymatic amplification. Detection is carried out, after placing the biological samples in a solution in order to extract the nucleic acid, by enrichment with target sequences by putting the biological samples into contact with at least one pair of appropriate triggers, followed by at least one appropriate dilution of the obtained enrichment amplifying solution, and by putting a fraction of this solution into contact with at least one pair of triggers, followed by the detection of the obtained double-strand target nucleic acid copies. Applications in the diagnosis of genetic, infectious and tumoral diseases, in checking biological samples and in cell typing etc.

22 Claims, 3 Drawing Sheets

METHOD FOR DETECTING SPECIFIC NUCLEIC ACID SEQUENCES BY AMPLIFICATION IN HIGHLY DILUTE SOLUTION

This application is a Continuation of application Ser. No. 07/778,112, filed Dec. 11, 1991, abandoned, which was filed as International Application No. PCT/FR90/00410 on Jun. 12, 1990.

The present invention relates to a method for detecting low amounts of nucleic acids obtained by amplification, as well as to applications of same.

One of the first amplification methods described is the polymerase chain reaction (PCR) developed by SAIKI R. et al. (Science, 1985, 230, 1350). This technique makes it possible in particular to amplify double-stranded DNA sequences and is based on the cyclic activity of a DNA polymerase, which enzyme is capable of copying a DNA strand, used as template, to give a complementary strand by elongation of an oligonucleotide primer starting from the 3' OH end.

The PCR technique consists in carrying out n successive amplification cycles during which two primers direct the amplification of the double-stranded DNA sequence which they delimit.

An amplification cycle is composed of three stages which make it possible to successively perform denaturation of the DNA (95° C.), hybridisation of the primers (37°–55° C.) and extension of the DNA strands by a DNA polymerase.

The technological bases of PCR rest on two fundamental points:
- the use of two oligonucleotide primers, one which is complementary to the DNA+ strand, the other to the DNA– strand and whose 3' ends are opposite;
- the repetitive use of the activity of a suitable DNA polymerase.

PCR then enables the use, under suitable conditions, of all the sequences neosynthesised during the cycle n, as templates for DNA polymerase during the cycle (n+1). This results in an exponential amplification of the number of target nucleic acid sequences as a function of the number of cycles in comformity with the amplification curve which comprises an exponential phase where the amount Q of target sequences obtained may be linked to the quantity Qo of initial target sequences, to the amplification factor x and to the number of cycles n, by the following formula: $Q=Q_o(1+x)^n$.

PCR thus makes it possible to exponentially amplify thousands of times, nucleic acid sequences termed target sequences.

This amplification technique is more particularly described in European Patent Application CETUS 201 184, which specifies in particular that the two oligonucleotide primers used in PCR are preferably single-stranded and should be sufficiently long in order to prime the synthesis of the extension product in the presence of DNA polymerase.

A certain number of improvements or perfections to this technique have been proposed and in particular, in order to avoid the addition of enzymes at each cycle, a DNA polymerase capable of withstanding a temperature of 100° C., Taq polymerase, described in European Patent Application CETUS 258 017, is added from the beginning of the process and makes it possible to perform a high number of consecutive amplification cycles. Taq polymerase has made it possible on the one hand to automate the amplification process and, on the other hand, to increase the specificity of amplification.

Thus, PCR makes it possible to obtain, without cloning, considerable amplification of a nucleic acid sequence, termed target sequence, and therefore a considerable gain in sensitivity. The amplified target sequence thereafter is directly accessible to various analytical methods such as the dot-blot method, electrophoresis or sequencing. Two Patent applications (European Patent Applications CETUS No. 200 362 and No. 229 701) describe more particularly the combination amplification-hybridisation for detecting a nucleic acid sequence sought after in a sample.

Since then, variants and/or perfections designed to make the amplified sequence detection stage easier, have been proposed and concern in particular the primers and/or the probes used.

One of these perfections is the use of two different probes one of which, labelled, is termed detection probe and the other of which comprises a fragment which has an affinity for another component and is termed capturing probe [British Patent 2 169 403, French Patent 85 19394, KOHNE D. (American Clin. Review, November 1986), U.S. Pat. No. 4 486 539, European Patent Applications 70685 and 70687].

As a variant, the primers themselves are modified so as to enable the capturing of the hybrid formed (French Patent Application 88 03107, European Patent Application MOLECULAR DIAGNOSIS Inc., No. 297 379).

Another of these perfections is illustrated by the method described in European Patent Application Syntex, No. 300 796, which proposes a variant of PCR which increases the sensitivity of the latter in particular in the presence of very low amounts of nucleic acid without however increasing the specificity thereof.

However, the routine use of PCR has led to a major disadvantage associated with its extreme sensitivity, namely the appearance of false positives which proved to be associated, after careful analysis of results, mainly with contamination of the analytical sample by homologous sequences.

A certain number of articles, which have appeared during the last two years approximately, describe such cases of contamination and propose means for resolving them:

- Y.M.D. LO et al., reveal, in an article which appeared in the Lancet (1988, ii, 679), this disadvantage of the polymerase chain reaction due to its sensitivity and recommend, in order to palliate this major disadvantage, that particular care be taken in the preparation of the DNA template before amplification.

- R. A. GIBBS et al. give the following advice in an article which appeared in Genes & Development, 1989, 3, 1095–1098:isolate all the reagents used for carrying out the PCR, the equipments used for analysing the products obtained; to use screw stoppers and even to go as far as freezing the contents before carrying out the final reaction in order to avoid the formation of aerosols; to limit the number of amplification cycles to the minimum both in order to reduce the risk of amplifying small amounts of contaminants already present and in order to reduce the total amount of reaction products, and to have available sets of different pipettes for each task.

- G. SARKAR et al. propose, in an article which appeared in Nature, 1990, 343, 27, to treat the samples with UV rays before adding the DNA template to be amplified, in order to avoid contamination.

- S. KWOK et al. propose, in an article which appeared in Nature, 1989, 339,237–238, a certain number of "good laboratory practices" in order to control and to avoid contamination:to physically isolate the preparations and products for PCR (separate rooms, UV rays and the like); to autoclave the profiles used; to divide the reagents into small samples in order to avoid repeated pipetting; to use protective gloves; to avoid spillage; to use pipettes which do not produce aerosols and the like.

However, the suggestions proposed by the various aforementioned authors for avoiding contamination do not in any way anticipate the problem of false positives due to amplification of heterologous sequences and/or the presence of cell debris.

Such heterologous sequences, which are different from the target sequences to be detected but nevertheless of sufficiently related structures to cause imperfect hybridisation between the specific primers of the target sequences to be detected and these heterologous sequences, are exponentially amplified like the target sequences, during PCR.

Indeed, none of the prior art methods of amplification and/or detection of specific nucleic acid sequences, which are the only ones easily automatable, makes it possible:

1. to eliminate the heterologous sequences exponentially amplified during the PCR as a direct consequence of the physical integration of primers in the neosynthesised strands, the amplification of these heterologous sequences leading to the emergence of false positives; and/or
2. to carry out a detection of nucleic acid in a homogeneous phase, that is to say not requiring either separation by gel electrophoresis, or fixation on a solid binding support, or use of modified nucleotide primers, or a hybridisation stage with a detection probe.

Accordingly, the aim of the Applicant therefore was to provide a qualitative, semi-quantitative as well as quantitative method for detecting and for identifying low amounts of nucleic acids by amplification, in particular in a homogeneous phase, which better meets the requirements of practical use than the prior art methods, in particular in that it is easy to automate, it is specific, sensitive, fast and economical and in that the presence of heterologous sequences and/or cell debris have practically no influence on the said detection.

DETAILED DESCRIPTION OF THE PREFERRED EMBODIMENTS

The subject of the present invention is a method for detecting specific nucleic acid sequences (a single sequence and/or a mixture of nucleic acid sequences) present in a biological sample, comprising at least one enzymatic amplification, characterized in that after suitably placing the biological sample in a solution in order to extract the nucleic acid or nucleic acids, the said method comprises the detection of a nucleic acids, the said method comprises the detection of a nucleic acid sequence or of a mixture of sequences using the following stages:

(1) a stage for enriching with the target sequence or sequences by:
(a) bringing the biological sample placed in a solution into contact with at least one pair of suitable primers in order to amplify at least one fragment of the said target nucleic acid sequence or sequences, the said primers being hybridised with the said target sequence or sequences and making it possible to obtain an amplifying solution for enrichment; and
(b) at least one suitable dilution of the amplifying solution for enrichment obtained in (a);

(2) a stage for detecting the amplified target sequences obtained by:
(c) bringing a fraction of the solution for enrichment obtained in (b) into contact with at least one pair of primers one of whose sequences, at least, is included in the target sequence amplified in (a); and
(d) detection of the double-stranded target nucleic acid copies obtained in (c), by any suitable means.

This latter amplification will be designated hereafter under the name "second series of amplifications".

In conformity with the invention, stages (a) and (b) are repeated at least once.

According to one advantageous embodiment of the invention, the dilution in stage (b) is between 1/50th and 1/100,000th.

According to an advantageous feature of this embodiment, the dilution in stage (b) is between 1/50th and 1/50,000th.

According to an advantageous embodiment of this feature, the dilution in stage (b) is between 1/50th and 1/10,000th, preferably between 1/200th and 1/5,000th.

This dilution makes it possible to initiate the amplification for detection starting with a biological material which is purified and which has the following properties:

it is, on the one hand, enriched with target sequences and it is, on the other hand, depleted of unwanted "parasite" sequences, namely of unused primers from stage (a), of heterologous sequences, of total nucleic acid with respect to the initial biological sample and of cell debris.

The fact that the unused primers from stage (a) are diluted, has the advantage of avoiding competition between the primers from stage (a) and the primers from stage (c) during the second series of amplifications. Furthermore, this makes it possible to use fewer primers during the second series of amplifications and to obtain a better yield of incorporation of the latter. This represents a major advantage because the primers for the amplification for detection are generally expensive and more difficult to synthesise.

This enrichment with target sequences by dilution of the amplifying solution in stage (a) makes it possible to put the heterologous sequences which cause false initiation of reading by defective hybridisation, and cell debris in conditions barely suitable for their amplification during the second series of amplifications and during the detection.

The process conforming to the invention in particular has the advantage of increasing the specificity of the assay by decreasing the amount of residual nucleic acid and various heterologous sequences derived from the biological sample.

In conformity with the invention, the primers in stage (a) are single-stranded nucleotide sequences (single primer (Ps)) which are hybridised with a target sequence.

Such primers optionally may be modified. This makes it possible to obtain where appropriate either a capturing primer or a detection primer.

Furthermore, in conformity with the invention, the primers in stage (c) are pairs chosen from the group which comprises the pairs: primer modified by a capturing system-primer modified by a detection system (Pc-Pd), the pairs: single primer-single primer (Ps1-Ps2), the pairs: single primer-primer modified by a capturing system (Ps1-Pc) and the pairs: single primer-primer modified by a detection system (Ps1-Pd).

Capturing primer (Pc) is understood as meaning a single-stranded nucleic acid sequence modified in particular by at least one affinity pair moiety and which is hybridised with a target sequence; for example, one or more biotins may be attached to one end of the oligonucleotide chain. The capturing primer may also be a branched oligonucleotide.

A detection primer (Pd) is understood as meaning a single-stranded nucleic acid sequence modified by a detection system which is hybridised with a target sequence; for example, the 5' end of the oligonucleotide may be labelled by a phosphorus 32.

According to another advantageous embodiment of the invention, the amount of primers used in stage (c) (second series of amplifications) is substantially lower than the amount of primers used in stage (a).

According to an advantageous feature of this embodiment, the amount of primers used in stage (c) is at least five times smaller than the amount of primers used in stage (a).

The number of cycles in the second series of amplifications is in particular chosen as a function of the dilution and the nature of the sample so as to confer an exponential character to this second series of amplifications.

According to another advantageous embodiment of the invention, when the pair of primers in stage (c) contains a capturing primer, the detection stage (2) comprises:

(d) bringing the amplifying solution for detection into contact with a suitable support which captures the nucleic acid fragments bearing the inserted capturing primer (Pc); and (e) the detection of the double-stranded target nucleic acid copies retained on the said support, by any suitable means.

This detection may be performed either by means of a detection probe (detection primer or subsequent hybridisation with a suitably labelled probe).

For such an embodiment, the capturing system is advantageously an affinity pair moiety. Such a system will enable the oligonucleotide to bind to the support bearing the other affinity pair moiety.

The following pairs may be mentioned in particular as affinity pairs: biotin-avidin or streptavidin, heavy metal derivative-thio group, various homopolynucleotides such as poly dG-poly dC, polydA-poly dT and poly dA-poly dU as well as various oligonucleotides of specific sequences such as in the case, for example, of branched primers, and the antigen-antibody pairs. Other pairs of components may also be used if they exhibit a sufficiently high affinity to enable the specific capturing to the solid support of the capturing primers ($P_c$) incorporated into the copies of the target nucleic acid; ligands and conjugates may be part of an affinity pair.

The detection system is advantageously chosen from the group which comprises isotopes ($^{125}I$, $^{35}S$, $^{32}P$), fluorophores, a lanthanide-type fluorescent system, a colorimetric enzymatic system (alkaline phosphatase, peroxydase), a fluorimetric, luminescent, bioluminescent or electrochemical enzymatic system and compounds which interact with a double-stranded nucleic acid, in particular a dye substance or an intercalating agent.

According to one feature of this embodiment, when a detection primer (Pd) is inserted in a target nucleic acid strand in stage (c), the detection in stage (e) is carried out by means of the said detection primer (Pd).

According to another feature of this embodiment, and when a single primer (Ps) is inserted in a strand in stage (c), the detection in stage (e) is carried out either by hybridisation of the double-stranded target nucleic acid copies retained on the support with a suitable detection probe, or by bringing into contact with a compound which interacts with the double-stranded target nucleic acid, in particular a dye substance or an intercalating agent capable of producing spectral modifications, and then detecting the said spectral modifications of the compound which interacts with the double-stranded nucleic acid by any suitable means.

According to another embodiment of the method conforming to the invention, when the pair of primers in stage (c) does not contain a capturing primer, the detection stage (2) comprises:

(d) the direct detection in a homogeneous liquid phase of the said amplified target sequences by bringing the double-stranded nucleic acids obtained after stages (a), (b) and (c) defined above, into contact either with a suitable detection probe, or with a compound which interacts with a double-stranded nucleic acid, in particular a dye substance or an intercalating agent capable of producing spectral modifications, and then detecting the said spectral modifications of the compound which interacts with the double-stranded nucleic acid by any suitable means.

According to one advantageous feature of this embodiment, the said compound is chosen from substances exhibiting a physicochemical modification after binding to the double-stranded DNA.

4',6-Diamidino-2-phenylindol-2 (DAPI), bisbenzimide, ethidium, 9-aminoacridine, proflavine, quinacrine, chloroquine, lucanthone, hycanthone, tilorone, m-AMSA, daunomycin, adriamycin, actinomycin D, 9-OH N-methyl-ellipticin, mitoxanthrone, bleomycin, echinomycin, ditercaline and the derivatives of these compounds, HOECHST 33 as well as suitably modified nucleotides, may be mentioned by way of non-restrictive examples of such compounds.

According to one advantageous embodiment of this feature, the compound capable of producing spectral modifications is a fluorescent intercalating agent such as, in particular, ethidium bromide or a bis-benzimide such as HOECHST 33-258.

Such an embodiment has the advantage of only requiring a direct measurement of the total labelled double-stranded nucleic acid present in the solution in order to characterise the desired sequence.

Such an embodiment in addition has the advantage of eliminating the competition reactions which occur in the prior art methods requiring fixation on a support of the double-stranded extension product obtained for the detection of the nucleic acid.

According to another advantageous feature of this embodiment, the successive dilutions of a test DNA and, in particular, a test viral DNA are subjected to a first series of amplifications in a suitable volume containing at least two target sequences capable of serving as templates, the four deoxyribonucleoside triphosphates and a suitable amount of Taq DNA polymerase, in a suitable buffer solution at pH 8.3 containing a small amount (of the order of 0.01% w/v) of gelatin, the products from the first series of amplifications thereafter being subjected to a second dilution stage, then to a second series of amplifications in an amplification medium which is advantageously similar to the one used in the first series of amplifications and which contains at least two target sequences capable of serving as templates, after which the compound capable of producing spectral modifications is added to the amplifying solution obtained after the second series of amplifications in order to detect the double-stranded vital DNA which may be present in the solutions.

The method conforming to the present invention exhibits a certain number of advantages compared to prior art methods:

increased specificity;

background reduction;

increased sensitivity given that the sample is highly diluted after the enriching amplification; in effect, this high dilution makes it possible:

to be in the exponential phase of the amplification most of the time for the target sequences alone, that is to say when the amount Q of target sequences obtained may be linked to the amplification factor x and to the number of cycles n by the formula $Q=Q_o (1+X)^n$;

to have a ratio of target sequences/nonspecific sequences substantially higher than 1 from the onset of the detection amplification;

to reduce the competition reactions associated with the extension products of heterologous nucleic acids and with components present in the biological medium (cell debris, proteins, natural biotin, initial total nucleic acid and the like).

The process conforming to the invention also makes it possible to carry out, during the detection amplification, simultaneously and in the same test tube, the detection amplification of several target sequences provided that branched oligonucleotides are used as capturing primer. The duplexes comprising branched oligonucleotides have a free single-stranded DNA strand. This free single-stranded DNA strand makes it possible to perform selective fixation by means of a complementary oligonucleotide attached to a support.

In addition, it should be emphasised that the dilution carried out after the first amplification makes it possible to work with a fairly low primer concentration in order to eliminate the occurrence of the phenomenon of dimerisation and amplification of primers which could lead to a parasite signal; furthermore, the dilution makes it possible to use fewer primers and therefore to have a better specificity in the detection phase of the detection amplification.

The process conforming to the invention is in particular applicable to the detection of genetic diseases, infectious diseases (viruses, parasites, fungi, bacteria and the like) and human, animal and also plant tumoral diseases, to the checking of biological samples and also to cell typing.

In addition, the subject of the present invention is a box, a kit or a coordinated set, ready for use, for implementing the method conforming to the invention, characterised in that in addition to the necessary amounts of suitable buffers and reagents for implementing the said detection, it comprises at least:

suitable doses of at least one first pair of suitable primers for implementing stage (a) of the said method;

suitable doses of at least one second pair of suitable primers for implementing stage (c) of the said method; and optionally suitable doses of a suitable probe for implementing stage (e) of the said method and/or suitable doses of at least one compound which binds in a non-covalent manner to a double-stranded nucleic acid such as, in particular, a dye substance or an intercalating agent capable of producing spectral modifications when it is attached to a nucleic acid or when it is not attached to a nucleic acid.

In addition to the preceding features, the invention also comprises other features which will emerge from the following description which refers to examples of implementation of the method which is the subject of the present invention.

It should be clearly understood however that these examples are given solely as illustration of the subject of the invention and do not constitute in any manner a limitation thereof.

In the following examples, Examples 1 to 8 describe embodiments of the hybridisation test conforming to the invention and Examples 9 to 11 describe embodiments in a homogeneous phase (detection in the presence of an intercalating agent).

I—Examples of the embodiment in solution.

A) Detection by a radioactive compound:

EXAMPLE 1

Detection of the type 16 human papilloma virus (HPV 16) by means of the process conforming to the invention using two single primers (Ps1 and Ps2) for the enriching amplification and a pair of primer Pd-Pc for the detection amplification.

During the hybridisation test conforming to the invention, the number of cycles during the enriching amplification, the dilution and the number of cycles during the detection amplification depend on the target sequence to be amplified and to be detected, on the dilution and on the nature of the sample.

The enriching amplification may comprise by way of non-restrictive example, between 20 and 40 cycles, the dilution may be between 1/200th and 1/100,000th and the detection amplification may comprise 3 to 15 cycles; in this case, the primer concentrations during the detection amplification are ten times lower than those during the enriching amplification while obtaining a very high primer incorporating level (about 75%) in the final product.

Another example of implementation of the process conforming to the invention comprises two series of enriching amplification which, by way of non-restrictive example, may be considered as follows:

1st enriching amplification (10–40 cycles), 1/200th dilution;

2nd enriching amplification from the solution obtained (10–40 cycles), 1/1000th dilution;

detection amplification (3–15 cycles).

Preparation of the support:

The supports used here are finned polystyrene tubes coated in a first instance with bovine serum albumin (BSA) coupled to biotin and then, in a second instance, with avidin.

5 g of BSA-biotin in 500 µl of phosphate buffer (0.05M, pH 7.3) are incubated for 2 hours at room temperature in finned tubes. The liquid is removed and replaced with 500 µl of a solution of avidin at 5 mg/ml in the same buffer and incubated for two hours at room temperature. The free sites on the support are then blocked with a solution at 20 µg/ml of denatured and sonicated herring sperm DNA. The tubes may be preserved in this medium for several weeks at +4° C.

Enriching amplification:

The test DNA solution is subjected to the first amplification in a medium containing a total volume of 50 μl:50 pmol of each of the two primers Ps1 and Ps2, 300M of each of the four deoxyribonucleoside triphosphates (that is to say dATP, dCTP, dGTP and dTTP) (Boehringer Mannheim), 1.5 mM of $MgCl_2$, 50 mM of KCl, 10 mM of tris-HCl, pH 8.9, 0.01% (W/V) of gelatin and 2.5 units of Taq DNA polymerase (Amersham). Thirty amplification cycles are performed by means of an automated apparatus (one cycle corresponding to 90 s of denaturation at 92° C., 90 s of annealing at 50° C. and 120 s of extension at 72° C.).

Detection amplification:

2 μl of each sample previously amplified in a volume of 50 μl are diluted in 400 μl of water. 2 μl of this solution (that is to say 1/5000th of the enriching amplification) are then subjected to the detection amplification consisting of 12 cycles, in a total volume of 25 μl in the amplification medium previously described, in the presence of the modified primers:. either 5 pmol of 5'-biotinylated oligonucleotide, Pc3 and 5 pmol of 5' $^{32}$P-labelled Pd4 oligonucleotide, the specific activity of the said probe being deliberately limited to 50,000 cpm/pmol; the total activity per sample is about 250,000 cpm.

Figure 1:
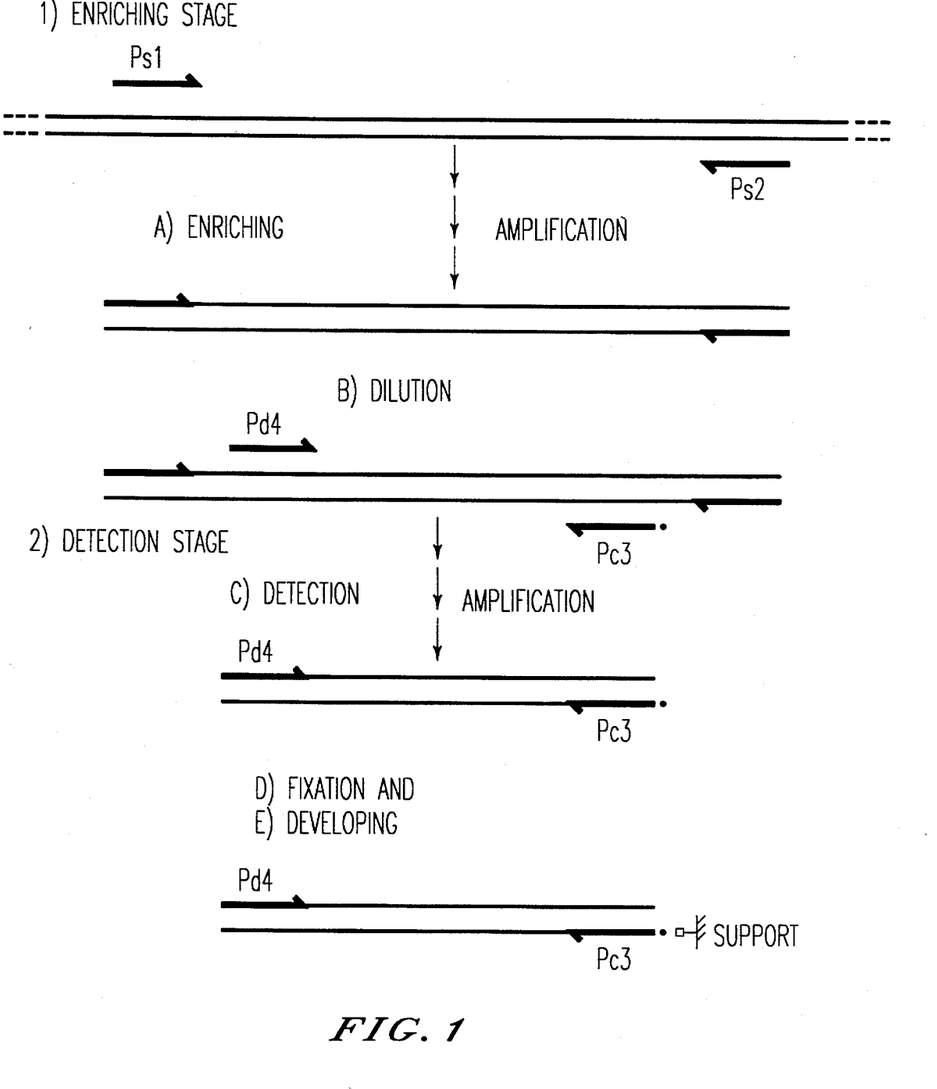
FIG. 1 illustrates the method according to the present invention, comprising:
enriching the sample with the sequence to be detected by carrying out a first PCT with two primers, Ps1 and Ps2, diluting the obtained solution,
carrying out a second amplification with two primers, Pd4 and Pc3,
fixing and detecting the sequence by using the label of Pd4.
Figure 2:
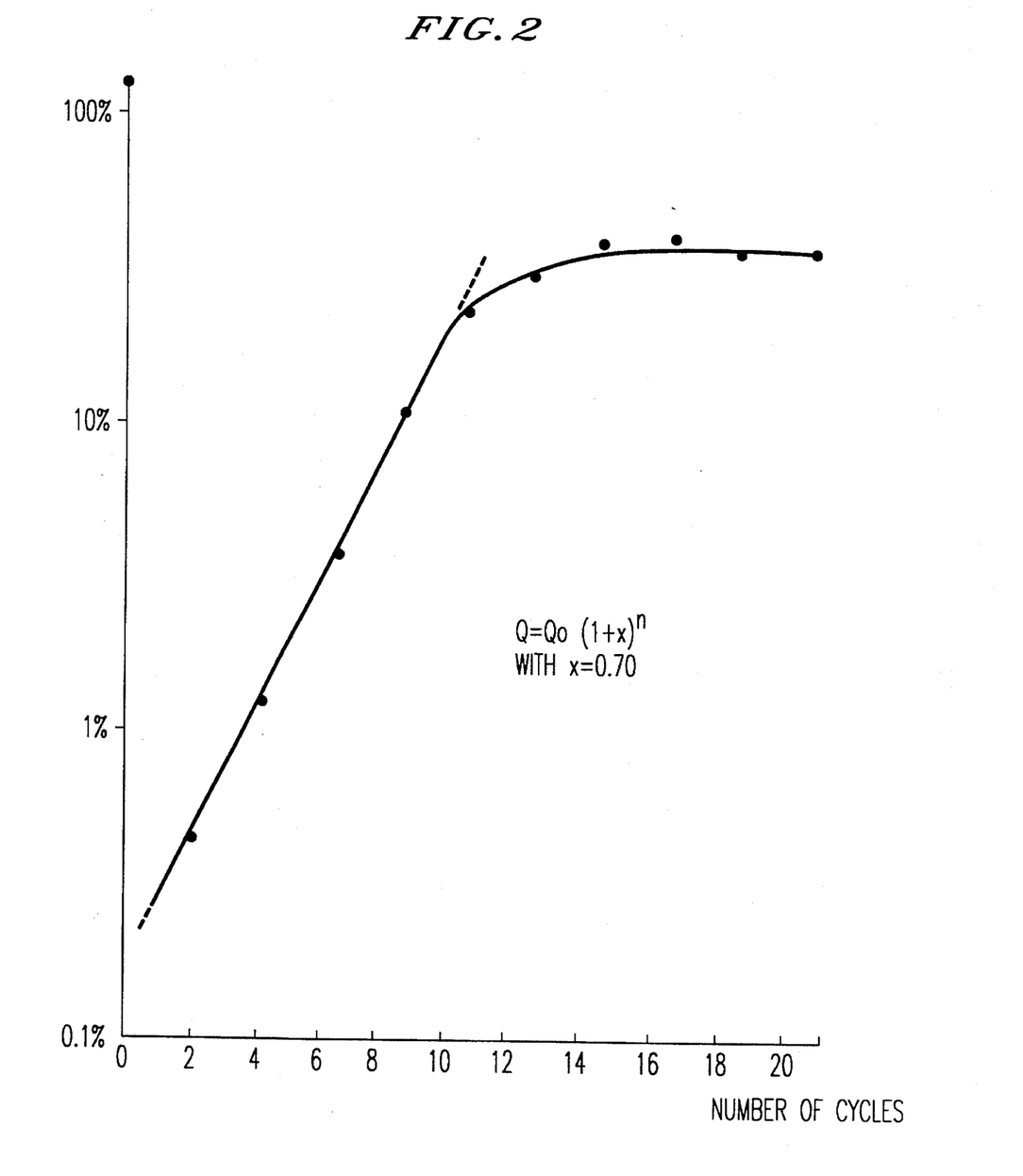
FIG. 2 is a study of the kinetics of detection amplification of the method according to example 1; 12–15 cycles are sufficient to provide a good detection. The factor "x" in the formula $(1+x)^n$ corresponding to the amplification yield was estimated to be about 0.70 between cycle 0 and cycle 10. In the graph, the x-axis represents the number of cycles, and the y-axis represents the fixation percentage.

FIG. 1 shows the principle behind the method described in Example 1. The pair of primers in the enriching amplification is represented by the single primers Ps1 and Ps2; the pair of primers in the detection amplification is represented by the 5' $^{32}$P-labelled primers, Pd4 and the biotinylated primer, Pc3.

Fixation on tube and detection of the DNA produced:

All the 25 μl obtained from the detection amplification is transferred in an avidin-coated tube containing 475 μl of ST fixation buffer (0.5M NaCl, 50 mM tris-HCl, pH 9.5). The fixation is carried out for one hour at 50° C. The tubes are then emptied and rinsed with 1 ml of ST-1% Tween 20, once for 5 min at room temperature, once for 5 min at 50° C. and once for 5 min at 50° C. with 1 ml of 0.1×ST-1% Tween 20.

The radioactivity retained on the tubes is then directly counted by Cerenkov counting. The results are expressed by the ratio "R" of the activity retained in the tube over the initial total activity (that is to say about 250,000 cpm).

EXAMPLE 2

Detection of the type 16 human papilloma virus (HPV 16) by means of the method conforming to the invention using two single primers Ps1 and Ps2 for the enriching amplification, a pair Ps3-Ps4 for the detection amplification and a probe Pd5 for the detection.

The procedure is as in Example 1; the difference relates to the pair of primers for the detection amplification and to the detection.

The oligonucleotide Ps4 is not labelled and the detection is achieved, after denaturation of the sample at 100° C., by hybridisation with 0.1 pmol of 5' $^{32}$P-labelled probe, Pd5 (35-mer). The specific activity of the probe is high (2.5×10$^6$ cpm/pmol) and the total activity per sample is about 250,000 cpm.

The labelled detection probe Pd5 is added after transferring the amplifying solution for detection in an avidin-coated tube containing 475 μl of ST fixation buffer as specified in Example 1.

EXAMPLE 3

Detection of HPV 6DNA in suspected biopsies of the neck of the uterus.

DNA from biopsies is conventionally extracted with phenol-chloroform after lysis of the cell and digestion of the proteins (Maniatis et al., Molecular cloning, A laboratory manual, Cold Spring Harbor Laboratory, 1982). Of the 12 samples, 4 were strongly positive (R>25%), 3 were positive (R>10%); the negatives maintaining a very low background (R<1%) (R being the ratio of the activity retained in the tube over the initial total activity). The values obtained from this technique conforming to the invention correlate with the results obtained by conventional hybridisation on filter but, surprisingly, exhibit a substantially higher sensitivity.

EXAMPLE 4

Detection of HPV 16 in vaginal swabs.

The vaginal swabs are simply resuspended in sterile PBS and then centrifuged. The pellet is taken up in 200 μl of water and heated at 100° C. for 15 min. The supernatant is recovered and frozen at −20° C. Of the 8 samples treated according to the procedure previously described (Example 1), only one turned out to be weakly positive (R=2.5%) with the others having an activity which was comparable to that of the negative controls (R<1%); these results still correlate with those obtained by the filter hybridisation technique.

EXAMPLE 5

Use of an $^{125}$iodine-labelled primer.

DNA from cells infected with the HPV 16 virus and DNA from non-infected cells, used as negative control, were subjected to an enriching amplification according the procedure described in Example 1.

After diluting 5000-fold, the detection amplification is carried out in the presence of the biotinylated capturing primer, Pc and a 5' $^{125}$iodine-labelled detection oligonucleotide, Pd according to the technique described in French Patent 88 08240. The labelling is deliberately limited to a low specific activity (375,000 cpm/mol). The detection of the duplex is carried out according to the procedure used for a $^{32}$P-labelled primer described in Example 1. The double strand is fixed by the biotin on the avidin-coated tube. After rinsing, $^{125}$iodine is measured with a gamma counter.

| Results | Counting yield R | (cpm retained/ total cpm) |
|---|---|---|
| T1 (+) | (HPV16 positive DNA from biopsy) | 21.5% |
| T2 (+) | (HPV16 positive DNA from biopsy) | 16.5% |
| T (−) | HPV16 negative cell DNA) | 0.4% |
| Background in the absence of DNA | | 0.04% |

B) Non-radioactive detection:

EXAMPLE 6

Colorimetric detection on microtitre plates. Use of a primer bearing the dinitrophenyl group.

DNA from cells infected with the HPV16 virus and uninfected genomic DNA were subjected to an enriching amplification and then diluted according to the procedure described (see Example 1). The detection amplification is performed in the presence of the biotinylated capturing primer Pc and a primer Pd bearing the dinitrophenyl group introduced at the 5' end according to the technique described in French Patent 88 08240. The detection of the duplex comprises several stages:

1. Incubation for 1 hour at 37° C. with a rabbit anti-dinitrophenyl antibody (Sigma Chemical Co.) in a PBS buffer (phosphate buffered saline), 1% Tween 20, 1% BSA (bovine serum albumin).
2. Washings with 3×400 µl of PBS buffer, 1% Tween 20, 1% BSA, at room temperature.
3. Incubation for 1 hour at 37° C. with an alkaline phosphatase-coupled anti-rabbit antibody (Sigma Chemical Co.), diluted to 1/300th in the same buffer.
4. Three washings with PBS, 1% Tween 20, 1% BSA, at room temperature.
5. Detection by hydrolysis of the dinitrophenyl phosphate (Sigma kit). Reading at 405 nm.

| Results | OD | Signal/Noise |
|---|---|---|
| T1 (+) (HPV16 positive biopsy DNA) | 2.6 | 21.6 |
| T2 (+) (HPV16 positive biopsy DNA) | 1.9 | 15.8 |
| T (−) (HPV16 negative biopsy DNA) | 0.16 | 1.3 |
| In the absence of DNA | 0.12 | 1 |

EXAMPLE 7

Other examples of detection in solution by the method.

a) Amplifications:

Crude cell extracts were prepared from Hela (HPV 18+) and fibroblast (HPV−) cells:after centrifugation, the cell pellet is taken up in 250 µl of water and heated for ten minutes at 100° C. The cell debris are removed by a brief centrifugation and the supernatant containing the soluble nucleic acids is recovered.

An amplification for enriching with HPV18 is carried out in a conventional PCR medium in the presence of 50 pmol of each of the primers. It comprises 30 cycles:denaturation at 94° C. for 1 min 30, annealing at 50° C. for 1 min and extension at 72° C. for 1 min 30.

A detection amplification is performed using a 1/800th dilution of the enriching solution. This amplification is carried out using two modified primers:the first comprises a dinitrophenyl residue at the 5' end, that is the capturing primer, the second a biotin residue, that is the detection primer. The amplification medium contains 5 pmol of each primer in a total volume of 25 µl. The number of cycles is 18:denaturation at 94° C. for 1 min, annealing at 55° C. for 1 min and extension at 72° C. for 1 min.

b) Saturation of the tubes:

Small-model Startubes Nunc tubes are coated overnight at 37° C. with anti-DNP antibodies in 0.05M sodium carbonate/bicarbonate buffer, pH 9.5, 1 mMMgCl$_2$. The free sites are then saturated with a 2% solution of BSA in the same buffer for 3 hours at room temperature. The tubes are then washed for 5 minutes in PBS and preserved in this same buffer at 4° C.

c) Fixation of the amplification products:

15 µl of the detection amplification products are fixed in 500 µl of PBS for two hours at 37° C. A 5-min wash is then carried out in 500 µl of PBS/0.1% BSA/4% Tween 20 and then two 5-min washings in PBS.

A brief BSA saturation is then carried out (3% solution in PBS):one hour at 37° C. The product is washed for 5 min with PBS.

The avidin-alkaline phosphatase solution is allowed to react (1/12500th dilution in PBS). Fixation of this complex is carried out for thirty minutes at room temperature. It is followed by three 5-min washings in PBS.

d) Fluorescent detection:

The alkaline phosphatase substrate used is 4-methylumbelliferyl phosphate. Following cleavage of the phosphate by the enzyme, the substrate becomes fluorescent. The excitation wavelength is 374 nm and the fluorescence emission wavelength is 450 nm.

0.05M stock solution of substrate is prepared in 0.1M tris buffer, pH 9.5, 0.1M NaCl, 5 mM MgCl$_2$. The working solution is obtained by a 1/300th dilution of the stock solution. 500 µl of this solution are used per tube. The enzyme is allowed to react for 15 min and then the very intense blue fluorescence is measured.

Calibration of the fluorimeter: 0% on the buffer 100 % on positive DNA

Measurement on the negative DNA: 2%

Measurement on the blank: 2% e) Luminescence detection:

The substrate for luminescence is a dioxetane derivative:adamantyl-1,2-dioxetane phosphate. The luminescence directly depends on the action of the enzyme:the phosphate cleavage causes formation of an unstable anion which dissociates. This cleavage creates a new activated anion which produces the emitted light.

A stock solution at 10 mg/ml is available. This solution is diluted 100-fold in a 0.05M sodium carbonate/bicarbonate buffer, pH 9.5, 1 mMMgCl$_2$. 500 µl of this solution are used per tube. The enzyme is allowed to react for 10 min and then the light is measured in a luminometer.

Signal from the positive DNA: 245

Signal from the negative DNA: 4

Signal from the blank: 1.8

This detection method practically achieves the sensitivity values of radioactive methods. It is a method of choice for a non-radioactive detection.

f) Colorimetric detection:

The alkaline phosphatase substrate used is p-nitrophenyl phosphate. The loss of phosphate by enzymatic action leads to a yellow compound the optical density of which is measured at 405 nm.

Two tablets of phosphatase substrate, Sigma 104, are dissolved in 10 ml of 0.8M diethanolamine buffer, 5 mM MgCl$_2$, pH 9.8. 500 µl are used per tube. The enzyme is allowed to react for 10 minutes in darkness and the reaction is stopped by addition of 250 µl of 2N sodium hydroxide.

Measurement on the positive DNA: 0.32 OD

Measurement on the negative DNA: 0.02 OD

Measurement on the blank: 0.01 OD

II—Examples of the embodiment in homogeneous phase.

EXAMPLE 8

Detection of the type 16 human papilloma virus (HPV 16) DNA by means of the embodiment in homogeneous phase conforming to the invention.

The various solutions of test DNA were subjected to a first amplification in a medium containing in a total volume of 50 µl, 50 pmol of each of the two primers P1 and P2, 200 µM of each of the four deoxyribonucleoside triphosphates (that is to say dATP, dCTP, dGTP and dTTP) (Boehringer Mannheim), 1.5 mM of MgCl$_2$, 50 mM of KCl, 10 mM of tris-HCl, pH 8.3, 0.01% (W/V) of gelatin and 2.5 units of-Taq DNA polymerase (Amersham). Thirty cycles of amplification were carried out by means of an automated apparatus (one cycle corresponding to 90 s of denaturation at 94° C., 90 s of annealing at 50° C. and 120 s of extension at 72° C.).

1 µl of each previously amplified sample is diluted in 100 µl of water. 1 µl of each solution (1/2500th) is then subjected to a second series of amplifications of 15 cycles in a total volume of 25 µl, in the amplification medium previously described, and containing 5 pmol of the two primers, B1 and B2.

1 µl of ethidium bromide at 5 µg/ml (that is to say 5 ng) is added to 20 µl of amplifying solution; the mixture is stirred and then the tubes are examined under U.V. at 254 nm. Only the solutions containing HPV16 viral DNA emit a detectable fluorescence. This allows a rapid distinction to be made between the positive and negative samples.

The results obtained correspond to those obtained with the control gel.

EXAMPLE 9

Detection of HPV18 viral DNA contained in a plasmid.

Successive dilutions are prepared of pBr322 plasmid DNA containing HPV18 viral DNA or not. The following concentrations are thus obtained: 20, 10, 1 and 0.1 ng of DNA for 1 µl.

The eight DNA solutions thus obtained are subjected to amplification in a volume of 25 µl containing 3 pmol of each of the two primers $P_1$ and $P_2$, the four deoxyribonucleoside triphosphates (200 µM), 1.5 mM of $MgCl_2$, 50 mM of KCl, 10 mM of tris-HCl, pH 8.3, 0.01% (w/v) gelatin and 0.25 unit of Taq DNA polymerase. Fifteen cycles of amplification were carried out by means of an automated apparatus:denaturation at 94° C. for 1 minute 30, annealing at 55° C. for 1 minute 30 and then extension at 72° C. for 1 minute.

At the end of these fifteen cycles, 1 µl of ethidium bromide solution at 5 µg/ml (that is to say 5 ng) is added to each of the tubes, the mixtures are rapidly stirred and then the tubes are examined on a UV transilluminator at 254 nm.

The tubes containing the plasmid amplifying solutions with viral DNA (20, 10 and 1 ng) fluoresce substantially, the one containing 0.1 ng of plasmid with viral DNA fluoresces slightly and those containing the plasmid alone do not produce any signal.

The ethidium bromide detection of the product from the amplification of a highly purified and highly dilute DNA is carried out immediately after the amplification and gives a very significant result.

EXAMPLE 10

Other examples of direct detection in liquid medium:

1) Use of a bis-benzimide (called "HOECHST 33-258"):

a) Detection of the HIV virus DNA (Acquired Immuno Deficiency Syndrome).

1 µl of DNA from the lymphocytes or monocytes of healthy individuals or individuals carrying the virus, from the spleen of individuals carrying the virus or from plasmid containing an insert from the strain HIV1/lav, are subjected to a primary amplification in a volume of 50 µl as described in Example 1.

1 µl of each previously amplified sample is diluted in 200 µl of $H_2O$. 2 µl of this solution are subjected to a second amplification of 25 cycles in a final volume of 25 µl with the primers B1 and B2.

20 µl of this solution are then diluted in 1 ml of 50 mM tris-HCl buffer, pH 7.4, 2M NaCl, containing a final 1 µl of HOECHST 33-258.

After stirring, the fluorescence is measured in a Perkin Elmer LS5 spectrofluorimeter (excitation 360 nm, emission 450 nm). The apparatus is previously calibrated using various dilutions of double-stranded DNA.

Calibration series:

| 0.75 µg | 0.35 µg | 0.19 µg | 0.01 µg | 0 µg DNA |
|---------|---------|---------|---------|----------|
| 100%    | 30%     | 15%     | 9%      | 0%       |

Two sets of different primers are used in the tat gene and in the pol gene of HIV1.

|  | CONTROL $H_2O$ | LYMPHO+ | LYMPHO– | SPLEEN+ | PLASMID+ |
|---|---|---|---|---|---|
| SOLUTION | – | ++ | – | ++ | +++ |
| FILTER   | – | ++ | – | ++ | +++ |

|  | CONTROL $H_2O$ | LYMPHO+ | LYMPHO– | MONO+ | PLASMID+ |
|---|---|---|---|---|---|
| SOLUTION | – | ++ | – | + | +++ |
| FILTER   | – | ++ | – | – | +++ | b) Detection of the types 16 and 18 human papilloma virus DNA.

5 µl of a solution of HPV 18+ (HELA) and HPV 16+ (CASKI) cell supernatant, (106 cells in 250 µl of $H_2O$), and HPV-negative fibroblasts are subjected to an amplification as previously described. After a 200-fold dilution, 2 µl of this solution are subjected to a secondary amplification and examined by fluorescence.

Calibration series:

| 1.5 µg | 0.75 µg | 0.38 µg | 0.19 µg | 0.1 µg | 0 µg DNA |
|--------|---------|---------|---------|--------|----------|
| 100%   | 48%     | 20%     | 8%      | 2%     | 0%       |

| HPV 16: | | |
|---|---|---|
|  | CONTROL | FIBROBLASTS | CASKI |
| SOUTHERN | – | – | +++ |
| SOLUTION | – | – | +++ |

-continued

| | HPV 18: | | |
|---|---|---|---|
| | CONTROL | FIBROBLASTS | HELA |
| SOUTHERN | − | − | +++ |
| SOLUTION | − | − | +++ |

2) Use of DAPI:
a) Detection of HPV 18:

The procedure is as in the preceding example; two different dilutions are tested: 1/50 and 1/200.

The fluorescence is measured in a 5 mM tris-HCl buffer, pH 7.6, 8 mM NaCl, containing 0.2 µg/ml of DAPI (excitation 372 nm, emission 454 nm).
Calibration series:

| 1.5 µg | 0.75 µg | 0.38 µg | 0.19 µg | 0.1 µg | 0 µg |
|---|---|---|---|---|---|
| 100% | 50% | 24% | 12% | 6% | 0% |

| | HPV 18: | |
|---|---|---|
| | CONTROL | FIBROBLASTS |
| SOLUTION 1/200 | ++ | − |
| SOUTHERN | ++ | − | b) Detection of HIV1:
The procedure is as in the preceding examples.
Calibration series:

| | 2 µg | 1 µg | 0.5 µg | 0.25 µg | 0.12 µg | 0 µg |
|---|---|---|---|---|---|---|
| % | 100 | 48 | 20 | 10 | 6 | 0 µg |

| | HIV1: | | | |
|---|---|---|---|---|
| | CONTROL | LYMPHO+ | MONO+ | LYMPHO− | PLASMID+ |
| SOUTHERN | − | ++ | − | − | +++ |
| SOLUTION | − | ++ | + | − | +++ |

III—Role of the dilution stage (b).

Preliminary experiments have shown that a 1/10th dilution causes a high background with a low signal after capturing of the hybrids to the affinity template and this being independent of the number of cycles of the second series of amplifications. This may be due to the fact that the PCR is usually carried out in the presence of a high excess of primers and that after a 1/10th dilution, the amount of amplification primers still present in solution is high. During the second series of amplifications, competition is then produced between the amplification primers and the detection primers leading to a reduction in the efficiency of the PCR. High primer concentrations may also lead to the formation of dimeric primers.

Figure 3:
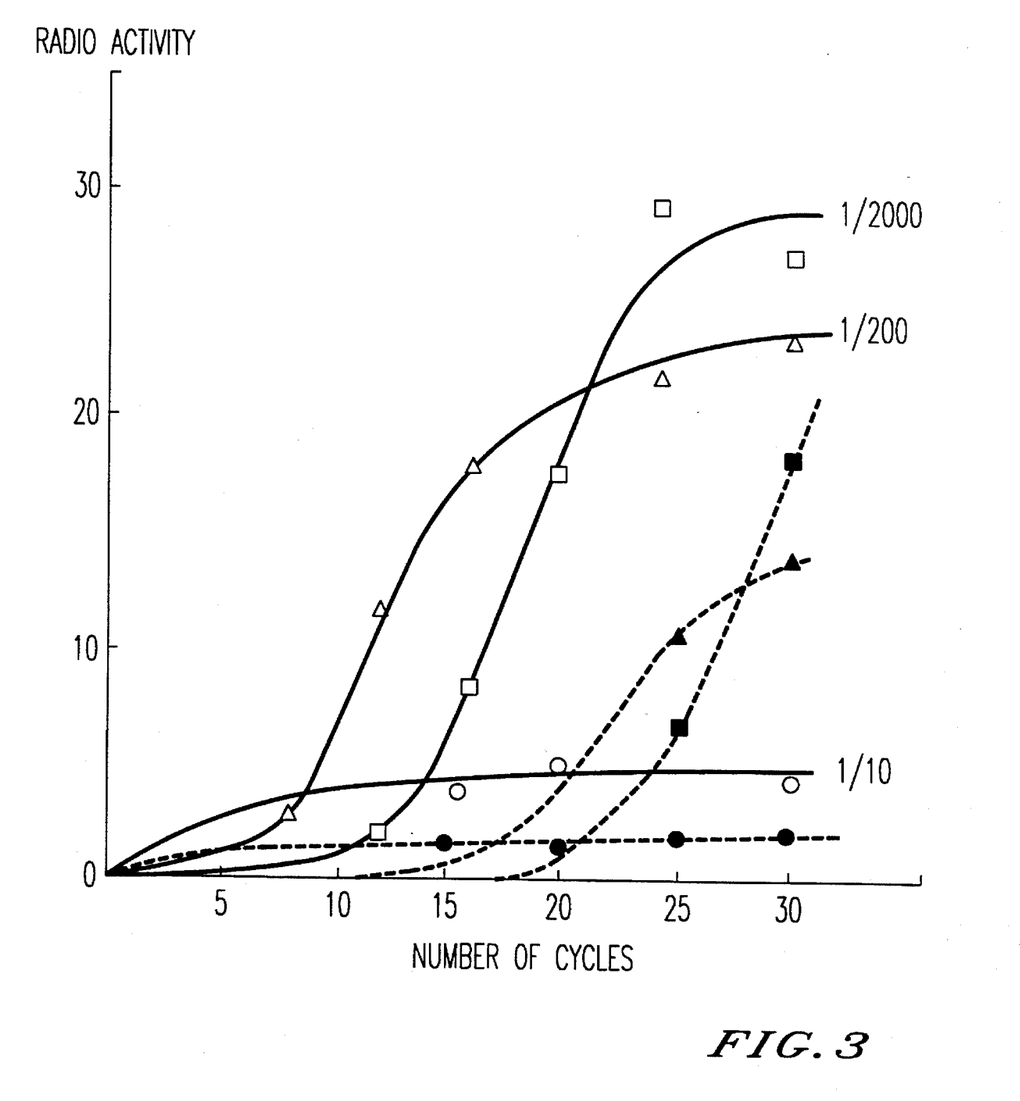
FIG. 3 illustrates the role of the dilution according to the present invention, wherein the x-axis represents the number of cycles, and the y-axis represents the fixation percentage. The dashed lines represent background.

The presence of cell debris may also lead to partial inhibition of the reaction when the PCR is performed on crude DNA samples and a 1/10th dilution is not enough to eliminate them. The background values are obtained by measuring the amplification of non-specific sequences. The specific signal is then defined as the number of counts from a specific amplification after subtracting the background value. The sensitivity of the procedure is estimated by measurement of the fixation percentage of the specific signal. The results are illustrated in FIG. 3. The sensitivity of detection is established as a function of the number of cycles.

FIG. 3 which comprises on the x-axis the number of cycles and on the y-axis the fixation percentage, shows PCRs performed on HPV 18+ Cells (Hela △, □,o) and the HPV 18-cells (BJAB, ■, ▲,●. The first amplification is performed on cells ($2\times10^4$) in a volume of 100 µl. After a 1/10th dilution (o, ●, a 1/200th dilution (△, ▲) and a 1/2000th dilution (□, ■), the samples are subjected to a second amplification in the presence of an iodine 125-labelled primer and a biotinylated primer. The hybrids are recovered and the radioactivity is measured. The total activity is 71,000 cpm/tube, the value represented is the percentage of radioactivity retained.

When the dilution is increased to 1/200th (△, ▲), and 1/2000th (□, ■) respectively, the number of copies of the target sequence present at the time of the second amplification are initially low and lead to a better efficiency of the PCR. The exponential phase is then more pronounced and the plateau is reached after 20 and 25 cycles respectively. In comparison, the background starts to increase exponentially after 16 and 20 cycles.

As is evident from the above, the invention is not in the least limited to the implementations, embodiments and applications which have just been described more explicitly; on the contrary, it embraces all the variants which may come to the mind of a specialist in this field without departing from the framework or the scope of the present invention.

We claim:

1. A method for detecting target nucleic acid sequences in a biological sample, comprising:

(A) extracting said nucleic acid or nucleic acids from said biological sample into a solution, (B) hybridizing said target nucleic acids in said solution with at least a first pair of primers, (B') amplifying said target nucleic acid to produce a solution, (C) diluting the solution to obtain a final dilution of from 1/2500th to 1/2,500,000th, (D) contacting the amplified target nucleic acid in the diluted solution with at least a second pair of primers, said second pair of primers having a nucleotide sequence which is included in said target nucleic acid, (D') amplifying the contacted amplified target nucleic acid to form a double-stranded target nucleic acid sequence; and (E) detecting said double-stranded target nucleic acid sequence.

2. The method of claim 1, wherein stages (B) and (C) are repeated at least once.

3. The method of claim 1, wherein the dilution in stage (C) is between 1/2500th and 1/250,000th.

4. The method of claim 1, wherein the amount of primers used in stage (D) is at least five times smaller than the amount of primers used in stage (B).

5. The method of claim 1, wherein the pair of primers of stage (D) contains a capturing primer, and the detecting stage (E) comprises:

bringing the solution of stage (D) containing target sequence copies into contact with a support which captures the nucleic acid fragments bearing the inserted capturing primer; and detecting the double-stranded target nucleic acid copies retained on said support.

6. The method according to claim 5, wherein the second pair of primers further contains a detection primer, and said detecting comprises detecting said detection primer.

7. The method of claim 1, wherein said first pair of primers is present in a concentration of from 0.2 to 1.2 pmol/µl.

8. The method of claim 1, wherein said second pair of primers is present in a concentration of from 0.0002 to 0.2 pmol/µl.

9. The method of claim 5, wherein said second pair of primers contains an unmodified primer inserted into said target nucleic acid or a nucleic acid complementary to said target nucleic acid, and said detecting is conducted by either:

(E-1) hybridizing the target nucleic acid copies retained on the support with a detection probe, or (E-2) contacting the target nucleic acid copies retained on the support with a dye substance or an intercalating agent, and detecting said dye substance or said intercalating agent.

10. The method of claim 1, wherein the first pair of primers are each single-stranded, unmodified primers which hybridize with said target sequence.

11. The method of claim 1, wherein the second pair of primers are a pair selected from the group consisting of: a capturing primer and a detection primer; a first unmodified primer and a second unmodified primer; an unmodified primer and a capturing primer; and an unmodified primer and a detection primer.

12. The method of claim 5, wherein the second pair of primers further contains an unmodified primer, and said detecting comprises (i) hybridizing the double-stranded target nucleic acid copies retained on the support with a detection probe, or (ii) bringing the double-stranded target nucleic acid copies into contact with a compound which interacts with the double-stranded target nucleic acid, and then detecting spectral modifications of the compound which interacts with the double-stranded nucleic acid.

13. The method of claim 1, wherein said second pair of primers does not contain a capturing primer, and said detecting comprises either (i) contacting said double-stranded nucleic acids with a detection probe in a homogeneous liquid phase or (ii) contacting said double-stranded nucleic acids with a compound which interacts with a double-stranded nucleic acid to produce spectral modifications, and detecting said spectral modifications.

14. The method of claim 3, wherein said compound which interacts with a double-stranded nucleic acid is a dye substance or an intercalating agent capable of producing spectral modifications.

15. The method of claim 14, wherein the compound which produces spectral modifications is a fluorescent intercalating agent.

16. The method of claim 15, wherein the fluorescent intercalating agent is ethidium bromide or a bis-benzimide.

17. The method of claim 13, wherein said amplifying steps are performed in a buffer solution at pH 8.3 containing about 0.01% w/v of gelatin, in the presence of at least two target sequences serving as templates and amounts of each of the four deoxyribonucleotide triphosphates and of Taq DNA polymerase sufficient to amplify said target sequences, and said detecting comprises adding said compound which interacts with said double-stranded nucleic acids to produce spectral modifications to a solution containing the double-stranded DNA, and detecting said spectral modifications.

18. The method of claim 12, wherein said compound which interacts with a double-stranded nucleic acid is a dye substance or an intercalating agent which produces spectral modifications.

19. The method of claim 17, wherein said target nucleic acid sequences are viral DNA sequences.

20. A method for detecting a target nucleic acid in a biological sample, comprising:

(A) extracting nucleic acids from said biological sample into a solution, (B) hybridizing said target nucleic acid in said solution with at least a first pair of primers, (B') amplifying said target nucleic acid to produce a second solution, (C) diluting the second solution obtained in (B') by a factor of from 1/200th to 1/100,000th, (D) contacting the amplified target nucleic acid in the diluted solution with at least a second pair of primers, said second pair of primers having a nucleotide sequence which is included in said target nucleic acid, (D') amplifying the contacted amplified target nucleic acid to form a double-stranded target nucleic acid sequence; and (E) detecting said double-stranded target nucleic acid sequence.

21. The method of claim 20, wherein said contacting step (D) comprises contacting from 1 to 2 parts by volume of said diluted solution with 25 parts by volume of a solution of said second pair of primers.

22. A method for detecting target nucleic acid sequences in a biological sample, comprising:

(A) extracting said nucleic acid or nucleic acids from said biological sample into a solution, (B) hybridizing said target nucleic acids in said solution with at least a first pair of primers in order to amplify at least one fragment of the said target nucleic acid sequence or sequences, (B') amplifying said target nucleic acid to produce a second solution, (C) diluting the second solution obtained in (B') by a factor of from 1/200th to 1/100,000th, (C') diluting the solution obtained in (C) by a factor of 1/25th, (D) contacting the amplified target nucleic acid in the solution obtained in (C') with at least a second pair of primers, said second pair of primers having a nucleotide sequence which is included in said target nucleic acid, (D') amplifying the contacted amplified target nucleic acid to form a double-stranded target nucleic acid sequence; and (E) detecting said double-stranded target nucleic acid sequence.

* * * * *

UNITED STATES PATENT AND TRADEMARK OFFICE
CERTIFICATE OF CORRECTION

PATENT NO. : 5,514,540
DATED : May 7, 1996
INVENTOR(S) : Robert TEOULE, et al.

It is certified that error appears in the above-indentified patent and that said Letters Patent is hereby corrected as shown below:

On the title page, Item [63], the Related U.S. Application Data, should read:

--Continuation of Ser. No. 778,112, filed as PCT/FR90/00410, Jun. 12, 1990, abandoned.--

Signed and Sealed this

Twentieth Day of August, 1996

*Attest:*

BRUCE LEHMAN

*Attesting Officer*  Commissioner of Patents and Trademarks